(12) United States Patent
Takeda et al.

(10) Patent No.: US 12,733,953 B2
(45) Date of Patent: Sep. 15, 2026

(54) ULTRASONIC PROBE

(71) Applicant: Canon Kabushiki Kaisha, Tokyo (JP)

(72) Inventors: Sakie Takeda, Nasushiobara (JP); Yasuhisa Makita, Nasushiobara (JP); Yuya Nagasaki, Nasushiobara (JP)

(73) Assignee: Canon Kabushiki Kaisha, Tokyo (JP)

( * ) Notice: Subject to any disclaimer, the term of this patent is extended or adjusted under 35 U.S.C. 154(b) by 186 days.

(21) Appl. No.: 18/518,802

(22) Filed: Nov. 24, 2023

(65) Prior Publication Data

US 2024/0173049 A1 May 30, 2024

(30) Foreign Application Priority Data

Nov. 30, 2022 (JP) ................................ 2022-191395

(51) Int. Cl.
*A61B 17/34* (2006.01)

(52) U.S. Cl.
CPC .. *A61B 17/3403* (2013.01); *A61B 2017/3409* (2013.01); *A61B 2017/3413* (2013.01)

(58) Field of Classification Search
CPC ............ A61B 17/3403; A61B 17/3409; A61B 17/3413; A61B 17/3488
See application file for complete search history.

(56) References Cited

U.S. PATENT DOCUMENTS

| | | | | |
|---|---|---|---|---|
| 6,132,379 A * | 10/2000 | Patacsil | .................... | A61B 8/13 600/459 |
| 2009/0247876 A1 | 10/2009 | Cannon, Jr. et al. | | |
| 2016/0113724 A1 * | 4/2016 | Stolka | ..................... | G06F 3/016 600/476 |

FOREIGN PATENT DOCUMENTS

JP 2002-191602 A 7/2002

OTHER PUBLICATIONS

Office Action issued Jun. 23, 2026, in corresponding Japanese Patent Application No. 2022-191395, 7 pages.

* cited by examiner

*Primary Examiner* — Michael T Rozanski
(74) *Attorney, Agent, or Firm* — Oblon, McClelland, Maier & Neustadt, L.L.P.

(57) ABSTRACT

An ultrasonic probe of embodiments includes a head part, an acoustic emission part, and a radiation part. The head part has a puncture guide configured to guide a puncture needle. The acoustic emission part is provided in the head part and configured to emit ultrasonic waves. The radiation part is configured to radiate laser beams in a first direction and a second direction different from the first direction. The first direction is opposite to a direction in which the acoustic emission part emits the ultrasonic waves.

6 Claims, 5 Drawing Sheets

ULTRASONIC PROBE

CROSS-REFERENCE TO RELATED APPLICATION

The present application claims priority based on Japanese Patent Application No. 2022-191395 filed Nov. 30, 2022, the content of which is incorporated herein by reference.

FIELD

Embodiments disclosed in the specification and drawings relate to an ultrasonic probe.

BACKGROUND

Laparoscopic surgery is performed by forming a plurality of small holes around a surgical site and inserting surgical instruments and diagnostic instruments such as an ultrasonic probe into the body through a cylindrical member called a trocar. For example, the tip of an ultrasonic probe used in laparoscopic surgery is provided with a puncture guide (a hole or groove for puncture), and an organ can be punctured at any angle by passing a puncture needle through the puncture guide.

In laparoscopic surgery, an ultrasonic probe is generally inserted into the body through a trocar, and a puncture needle is inserted directly from the body surface to access the puncture guide provided on the ultrasonic probe. However, the puncture guide is located on the back side hidden by the skin of a subject, making it difficult for a practitioner to visually recognize the puncture guide directly. For this reason, it is not easy for a practitioner to ascertain the position of the puncture guide and it becomes difficult to determine a puncture position at which a puncture needle will be disposed and a puncture angle at the time of inserting the puncture needle, and thus it is difficult to insert the puncture needle.

DETAILED DESCRIPTION

Hereinafter, an ultrasonic probe of embodiments will be described with reference to the drawings.

The ultrasonic probe of embodiments includes a head part, an acoustic emission part, and a radiation part. The head part has a puncture guide configured to guide a puncture needle. The acoustic emission part is provided in the head part and configured to emit ultrasonic waves. The radiation part is configured to radiate laser beams in a first direction and a second direction different from the first direction. The first direction is opposite to a direction in which the acoustic emission part emits the ultrasonic waves.

First Embodiment

Figure 1:
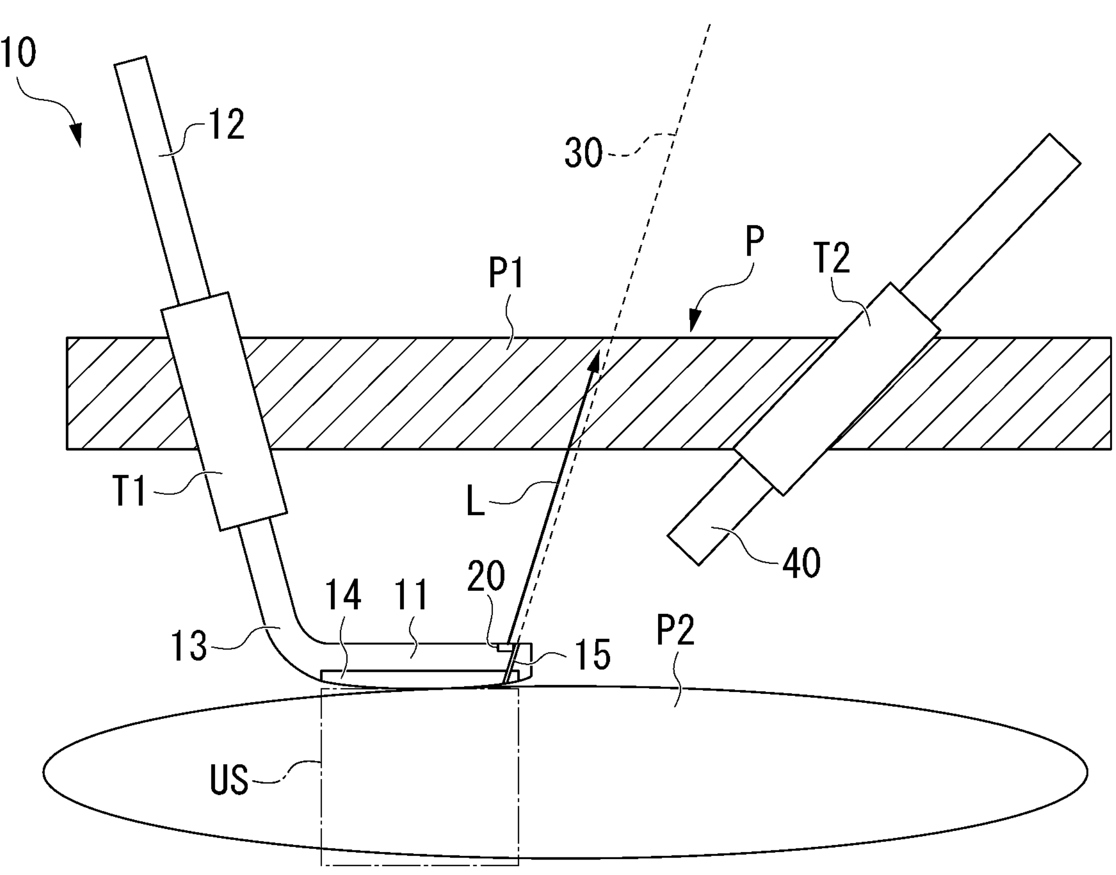
FIG. 1 is a diagram showing a state of an ultrasonic probe 10 of a first embodiment in use viewed from the side.

FIG. 1 is a diagram showing a state of an ultrasonic probe 10 of a first embodiment in use viewed from the side. The ultrasonic probe 10 of the first embodiment is used, for example, in laparoscopic surgery (hereinafter referred to as surgery). The ultrasonic probe 10 includes a radiation part 20. Surgery is performed using, for example, the ultrasonic probe 10, a puncture needle 30, an endoscope 40, a first trocar T1, and a second trocar T2.

While the surgery is being performed, a communication path is formed inside and outside the body of a subject P by the first trocar T1 and the second trocar T2. The ultrasonic probe 10 is introduced into the body of the subject P through the first trocar T1. The endoscope 40 is introduced into the body of the subject P through the second trocar T2. The puncture needle 30 is inserted into the abdominal wall P1 of the subject P. In FIG. 1, the puncture needle 30 is indicated by a broken line.

The ultrasonic probe 10 includes, for example, a transmitting/receiving head 11, a support part 12, a bent part 13, an acoustic emission part 14, and a radiation part 20.

A puncture hole 15 is formed in the transmitting/receiving head 11. The ultrasonic probe 10 is used, for example, to acquire an ultrasonic image of the inside of the body of the subject P when examining the subject P.

For example, a practitioner performs the surgery while holding the ultrasonic probe 10 with one hand and holding the puncture needle 30 with the other hand. In the following description, the side (top side) on which the practitioner inserts the puncture needle 30 from the transmitting/receiving head 11 will be referred to as a front side, and the side (bottom side) on which the puncture needle 30 advances will be referred to as a back side.

The transmitting/receiving head 11 is a plate-shaped member attached to the tip of the support part 12 via the bent part 13. The acoustic emission part 14 is provided inside the transmitting/receiving head 11. One end side of the transmitting/receiving head 11 is supported by the bent part 13. The puncture hole 15 is formed on the other end side of the transmitting/receiving head 11. The transmitting/receiving head 11 is disposed, for example, between the abdominal wall P1 and an organ P2 of the subject P at the time of performing surgery on the subject P. The transmitting/receiving head 11 is an example of a head part.

The support part 12 is an elongated member with a small diameter. The bent part 13 is connected to the tip of the support part 12. The support part 12 is connected to the base end of the bent part 13, and the transmitting/receiving head 11 is connected to the tip thereof. The transmitting/receiving head 11 is attached to the tip of the support part 12 via the bent part 13. By providing the bent part 13 between the support part 12 and the transmitting/receiving head 11, the transmitting/receiving head 11 can be placed along the surface of the organ P2.

The acoustic emission part 14 includes, for example, a plurality of ultrasonic elements arranged in an array direction and emits ultrasonic waves toward the organ P2.

An ultrasonic emission surface US is formed on the organ P2 side of the acoustic emission part 14. The acoustic emission part 14 receives reflected waves generated by radiated ultrasonic waves being reflected by the organ P2. The acoustic emission part 14 transmits reflected wave information based on the received reflected waves of ultrasonic waves to a control device. The control device generates an ultrasonic image on the basis of the transmitted reflected wave information. The ultrasonic image is, for example, an image showing a state of an acoustic emission surface when the subject P is cut from left to right.

Figure 2:
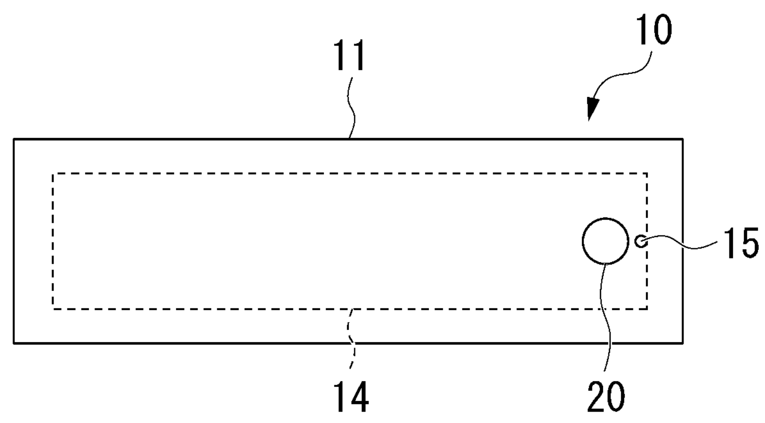
FIG. 2 is a diagram showing a state of the ultrasonic probe 10 of the first embodiment viewed from above.

The puncture hole 15 guides the puncture needle 30 operated by the practitioner. It is formed to penetrate the transmitting/receiving head 11. FIG. 2 is a diagram showing a state of the ultrasonic probe 10 of the first embodiment viewed from above. The puncture hole 15 is disposed at an end of the surface of the transmitting/receiving head 11 farther from the radiation part 20 when viewed from the bent part 13.

The puncture hole 15 is formed along a second direction such that the back side of the transmitting/receiving head 11 is closer to a curved part than the front side. A second light source 22 is provided such that a radiation direction of a second laser beam L2 is along an extending direction of the puncture hole 15. The puncture hole 15 is an example of a puncture guide.

Figure 3:
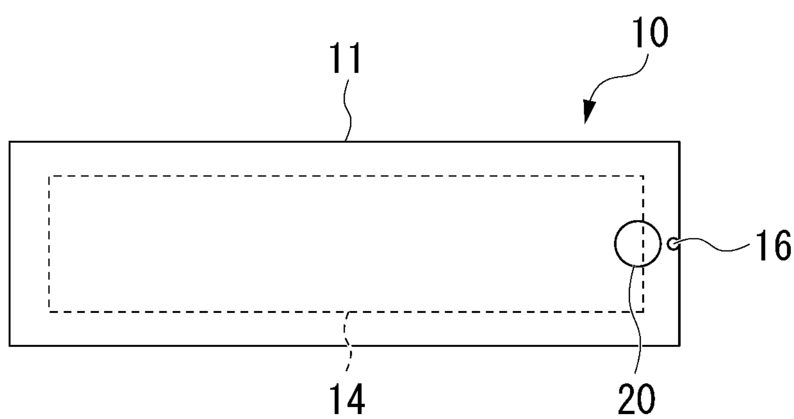
FIG. 3 is a diagram showing a state of an ultrasonic probe 10 of a modified example viewed from above.

The puncture guide may have a different form from the puncture hole 15 as in a modified example below. FIG. 3 is a diagram showing a state of an ultrasonic probe 10 of the modified example viewed from above. The puncture guide may be a puncture groove 16 shown in FIG. 3 instead of the puncture hole 15 shown in FIG. 2. A puncture groove 16 is formed in the transmitting/receiving head 11 of the ultrasonic probe 10 of the modified example. The puncture groove 16 is formed by cutting out the end portion of the transmitting/receiving head 11. A plurality of puncture holes 15 or puncture grooves 16 may be formed, or both the puncture holes 15 and the puncture grooves 16 may be formed.

Figure 4:
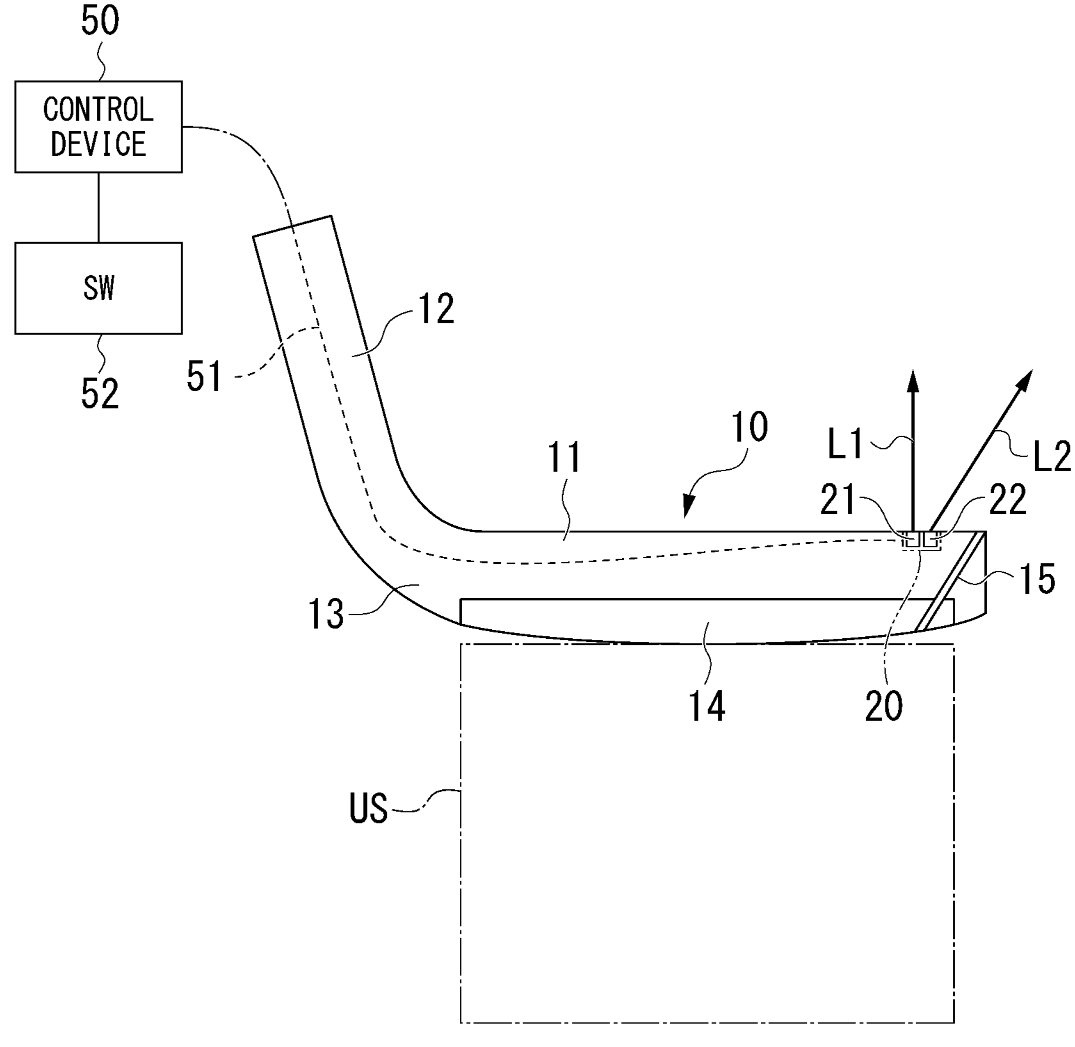
FIG. 4 is a diagram showing a state of the ultrasonic probe 10 of the first embodiment viewed from the side.

FIG. 4 is a diagram showing a state of the ultrasonic probe 10 of the first embodiment viewed from the side. The radiation part 20 is provided adjacent to the puncture hole 15 in the transmitting/receiving head 11 in the vicinity of the puncture hole 15. The radiation part 20 includes, for example, a first light source 21 and the second light source 22. The first light source 21 and the second light source 22 are arranged in parallel at positions close to each other.

The first light source 21 radiates, for example, a laser beam (hereinafter, a first laser beam) which is visible light in a direction (hereinafter, a first direction) opposite to the direction in which the acoustic emission part 14 emits ultrasonic waves. The first direction is, for example, on a straight line facing the direction in which the acoustic emission part 14 emits ultrasonic waves (hereinafter, a radiation direction), a direction opposite to the radiation direction.

The second light source 22 radiates, for example, a laser beam (hereinafter, a second laser beam) which is visible light in one direction (hereinafter, a second direction) different from the first direction. The second direction is, for example, a direction along the direction in which the puncture hole 15 extends, and is, for example, a direction having an inclination of less than 90°, for example, about 20° with respect to a straight line along the radiation direction. The second direction may be any other direction.

Figure 5:
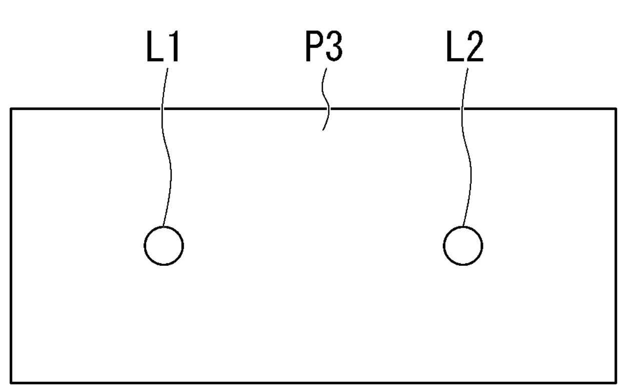
FIG. 5 is a diagram showing a state in which a first laser beam L1 and a second laser beam L2 are radiated to a body surface P3 in the first embodiment.

FIG. 5 is a diagram showing a state in which the first laser beam L1 and the second laser beam L2 are radiated to a body surface P3 in the first embodiment. While the first light source 21 and second light source 22 shown in FIG. 4 are close to each other, the radiation positions of the first laser beam L1 and the second laser beam L2 are spaced apart from each other on the body surface P3. The distance between the radiation positions of the first laser beam L1 and the second laser beam L2 is greater than the distance between the first light source 21 and the second light source 22.

The first laser beam L1 and the second laser beam L2 are displayed on the body surface P3 on the surface of the abdominal wall P1 (FIG. 1) by passing through the body surface P3 of the subject P. The radiation position of the first laser beam L1 displayed on the body surface P3 serves as a mark for the position of the puncture hole 15 on the front side of the transmitting/receiving head 11. The radiation position of the second laser beam L2 displayed on the body surface P3 is a position suitable for inserting the puncture needle 30.

The puncture needle 30 is a needle that is operated by the practitioner and inserted into internal organs and the like from outside the body in order to collect blood, body fluids, cells, and the like of the subject P. The endoscope 40 is a device with a small diameter equipped with a camera at the tip thereof. The endoscope 40 images the transmitting/receiving head 11 of the ultrasonic probe 10 and the puncture needle 30, for example. The endoscope 40 transmits images captured by the camera to the control device. For example, the control device displays the images transmitted by the endoscope 40 on a monitor or the like.

A control device 50 is electrically connected to the radiation part 20 via a wire 51. A switch 52 is electrically connected to the control device 50. The switch 52 is disposed at a position where the practitioner can operate the switch 52. The switch 52 can actuate (turns on) or stop operation of (turns oft) the radiation part 20 according to an operation of the practitioner.

The control device 50 outputs a control signal according to the operation of the switch 52 by the practitioner to the radiation part 20. In a case in which the practitioner performs an operation on the switch 52 to turn the radiation part 20 "ON" (hereinafter, an actuation operation), the control device 50 outputs an actuation signal to the radiation part 20. In a case in which the practitioner performs an operation on the switch 52 to turn the radiation part 20 "OFF" (hereinafter, a stop operation), the control device 50 outputs a stop signal to the radiation part 20.

In a case in which the control device 50 outputs an actuation signal when the first light source 21 and the second light source 22 do not radiate the first laser beam L1 and the second laser beam L2, the radiation part 20 starts radiation of the first laser beam L1 and the second laser beam L2 by the first light source 21 and the second light source 22. In a case in which the control device 50 outputs a stop signal when the first light source 21 and the second light source 22 radiate the first laser beam L1 and the second laser beam L2, the radiation part 20 ends radiation of the first laser beam L1 and the second laser beam L2 by the first light source 21 and the second light source 22.

The radiation part 20 may always radiate the first laser beam L1 and the second laser beam L2. The first light source 21 and the second light source 22 may radiate the first laser beam L1 and the second laser beam L2, respectively, or any one of the first light source 21 and the second light source 22 may radiate the first laser beam L1 or the second laser beam L2. The signal output by the control device 50 may be output to the radiation part 20 wirelessly.

The ultrasonic probe 10 of the first embodiment includes the radiation part 20 that radiates a laser beam L. Since the radiation part 20 is disposed near the puncture hole 15, the practitioner easily ascertains the position of the puncture hole 15 by visually recognizing the laser beam L that is radiated by the radiation part 20 and displayed by passing through the body surface P3 of the subject P. As a result, the practitioner can easily insert the puncture needle 30.

Further, the radiation part 20 includes the first light source 21 and the second light source 22, the first light source 21 radiates the first laser beam L1 in the first direction, and the second light source 22 radiates the second laser beam L2 in the second direction. The practitioner can easily confirm the position of the puncture hole 15 on the surface side of the transmitting/receiving head 11 by viewing the first laser beam L1 displayed on the body surface P3 of the subject P.

However, even if the position of the puncture hole 15 on the surface side of the transmitting/receiving head 11 is confirmed, it is conceivable that the practitioner is not sure about a position of the body surface P3 of the subject P at which the puncture needle 30 should be inserted if inclination of the puncture hole 15 is not known. In this regard, in the ultrasonic probe 10 of the first embodiment, the second laser beam L2 is radiated in the second direction. Therefore, the position on the body surface P3 of the subject P at which the puncture needle 30 will be inserted can be confirmed. Accordingly, it is possible to make it easier for the practitioner to insert the puncture needle 30.

Further, the second light source 22 radiates the second laser beam L2 along the extending direction of the puncture hole 15. Therefore, the puncture needle 30 is inserted toward the puncture hole 15 from the position indicated by the second laser beam L2 displayed on the body surface P3 of the subject P, and thus the puncture needle 30 is easily oriented in the direction in which the puncture hole 15 extends.

Accordingly, it is possible to easily insert the puncture needle 30 into the puncture hole 15, thereby making it easier for the practitioner to insert the puncture needle 30.

Second Embodiment

Next, an ultrasonic probe 10 of a second embodiment will be described. The ultrasonic probe 10 of the second embodiment differs from the first embodiment mainly with respect to the configuration of the radiation part. The second embodiment will be described below focusing on differences from the first embodiment. In the following description, the same elements as in the first embodiment may be denoted by the same reference numerals and the description thereof may be omitted.

Figure 6:
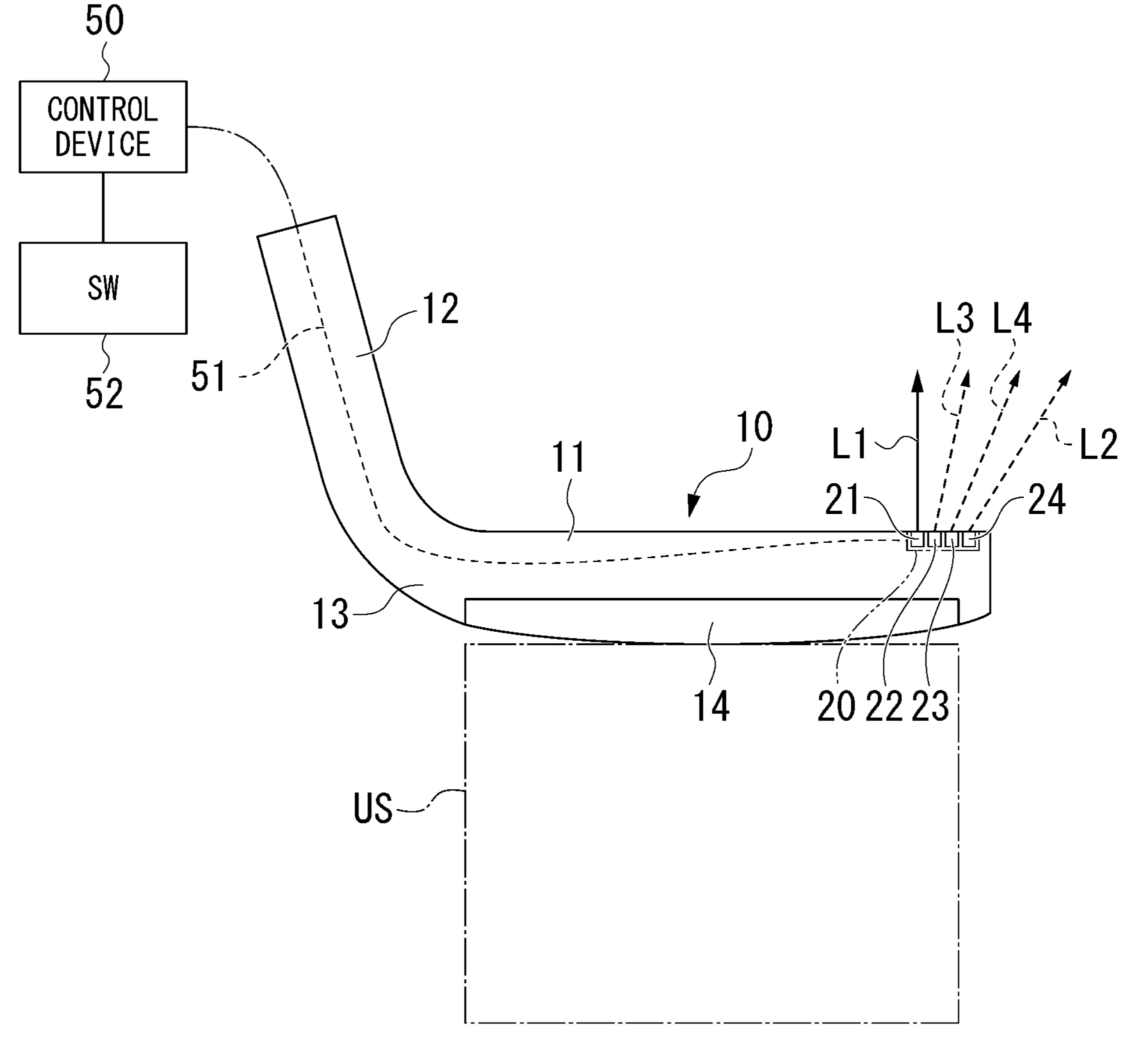
FIG. 6 is a diagram showing a state of an ultrasonic probe 10 of a second embodiment viewed from the side.

FIG. 6 is a diagram showing a state of the ultrasonic probe 10 of the second embodiment viewed from the side. In the ultrasonic probe 10 of the second embodiment, the radiation part 20 includes a first light source 21, a second light source 22, a third light source 23, and a fourth light source 24. Among the first light source 21 to the fourth light source 24, the first light source 21 is disposed at a position closest to the bent part 13.

The second light source 22 is disposed at the farthest position from the bent part 13 (a position closest to the tip of the transmitting/receiving head 11). The third light source 23 is disposed at a position next to the bent part 13 after the first light source 21, and the fourth light source 24 is disposed at a position next to the bent part 13 after the second light source 22 (between the second light source 22 and the third light sources 23).

The first to fourth light sources 21 to 24 radiate first to fourth laser beams L1 to L4 in different directions, respectively. The first direction is the direction in which the first light source 21 radiates the first laser beam, similarly to the first embodiment. In the second embodiment, a plurality of second directions are set. In the second embodiment, the second directions are directions in which the second to fourth light sources 22 to 24 radiate the second to fourth laser beams L2 to L4, respectively. The angle between the first laser beam L1 and the second laser beam L2 is, for example, the same as the angle between the first laser beam L1 and the second laser beam L2 in the first embodiment.

The radiation part 20 designates a direction in which a laser beam is radiated as a second direction from among a plurality of directions by designating a light source to radiate a laser beam together with the first light source 21 from among the second light source 22 to the fourth light source 24. The radiation part 20 including the second light source 22 to the fourth light source 24 is an example of a designation structure. The radiation part 20 may radiate a laser beam using any one of the second light source 22 to the fourth light source 24 without causing the first light source 21 to radiate a laser beam.

The angle between the first laser beam L1 and the third laser beam L3 is less than the angle between the first laser beam L1 and the second laser beam L2. The angle between the third laser beam L3 and the fourth laser beam L4 and the angle between the fourth laser beam L4 and the second laser beam L2 are the same as the angle between the first laser beam L1 and the third laser beam L3. The number of light sources provided in the radiation part 20 may be other than four, may be three, or may be five or more. The angles formed between adjacent light sources in the radiation part 20 may be the same or different.

Figure 7:
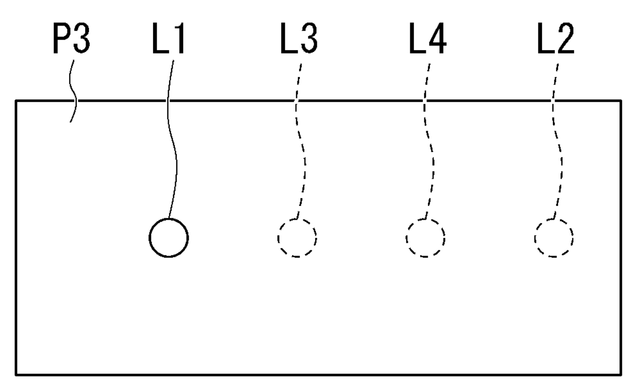
FIG. 7 is a diagram showing a state in which first to fourth laser beams L1 to L4 are radiated to the body surface P3 in the second embodiment.

FIG. 7 is a diagram showing a state in which the first to fourth laser beams L1 to L4 are radiated to the body surface P3 in the second embodiment. Both the first laser beam L1 and the second laser beam L2 are radiated to the same positions on the body surface P3 of the subject P as in the first embodiment. Both the third laser beam L3 and the fourth laser beam L4 are radiated to positions between radiation positions of the first laser beam L1 and the second laser beam L2 on the body surface P3 of the subject P. In the following description, the angles formed by the first laser beam L1 and the second to fourth laser beams L2 to L4 will be referred to as radiation angles of the second to fourth light sources 22 to 24.

A control device 50 similar to that of the first embodiment is connected to the radiation part 20 via a wire 51, and a switch 52 is connected to the control device 50. A practitioner can actuate the radiation part 20 or stop the operation of the radiation part 20 by operating the switch 52 and also select and designate a light source to be actuated or stopped from among the first light source 21 to the fourth light source 24.

The control device 50 outputs a designation signal to the radiation part 20 in a case in which the practitioner performs an operation on the switch 52 to designate a light source to be activated. The radiation part 20 designates a light source to be caused to emit a laser beam together with the first light source 21 from among the second light source 22 to the fourth light source 24 on the basis of the output designation signal. Therefore, the practitioner can designate the light source to be caused to emit a laser beam together with the first light source 21 and the second direction.

The ultrasonic probe 10 of the second embodiment has the same effects as the ultrasonic probe 10 of the first embodiment. Furthermore, in the ultrasonic probe 10 of the second embodiment, the radiation part 20 includes the first light source 21 to the fourth light source 24. Thereamong, the first light source 21 radiates the first laser beam L1 in the first direction, and the second light source 22 to the fourth light source 24 all radiate laser beams in the second direction different from the first direction.

The practitioner can designate the second direction by selecting a light source to emit a laser beam from the second light source 22 to the fourth light source and thus can designate a position at which the puncture needle 30 will be inserted into the body surface P3 of the subject P as a position desired by the practitioner. Therefore, it is possible to make it easier for the practitioner to insert the puncture needle 30.

In the second embodiment, the practitioner can designate the second direction by selecting the second light source 22 to the fourth light source 24, but the practitioner may designate the second direction in other aspects. For example, a mechanism for swinging a light source between the direction in which the second light source 22 faces and the direction in which the third light source 23 faces in the second embodiment may be provided such that the radiation angle of the second light source 22 can be changed to designate the second direction.

In the ultrasonic probe 10 of the second embodiment, the second light source 22 to the fourth light source 24 are provided as a plurality of light sources and a light source to emit a laser beam is selected from the plurality of light sources as an aspect in which the second direction in which a laser beam is radiated is selected from among a plurality of directions, but other aspects may be adopted. For example, the second direction may be designated from among a plurality of directions by providing an adjustment mechanism for adjusting a direction (angle) in which a laser beam is radiated by a light source and adjusting a laser beam radiation angle with the adjustment mechanism.

Third Embodiment

Figure 8:
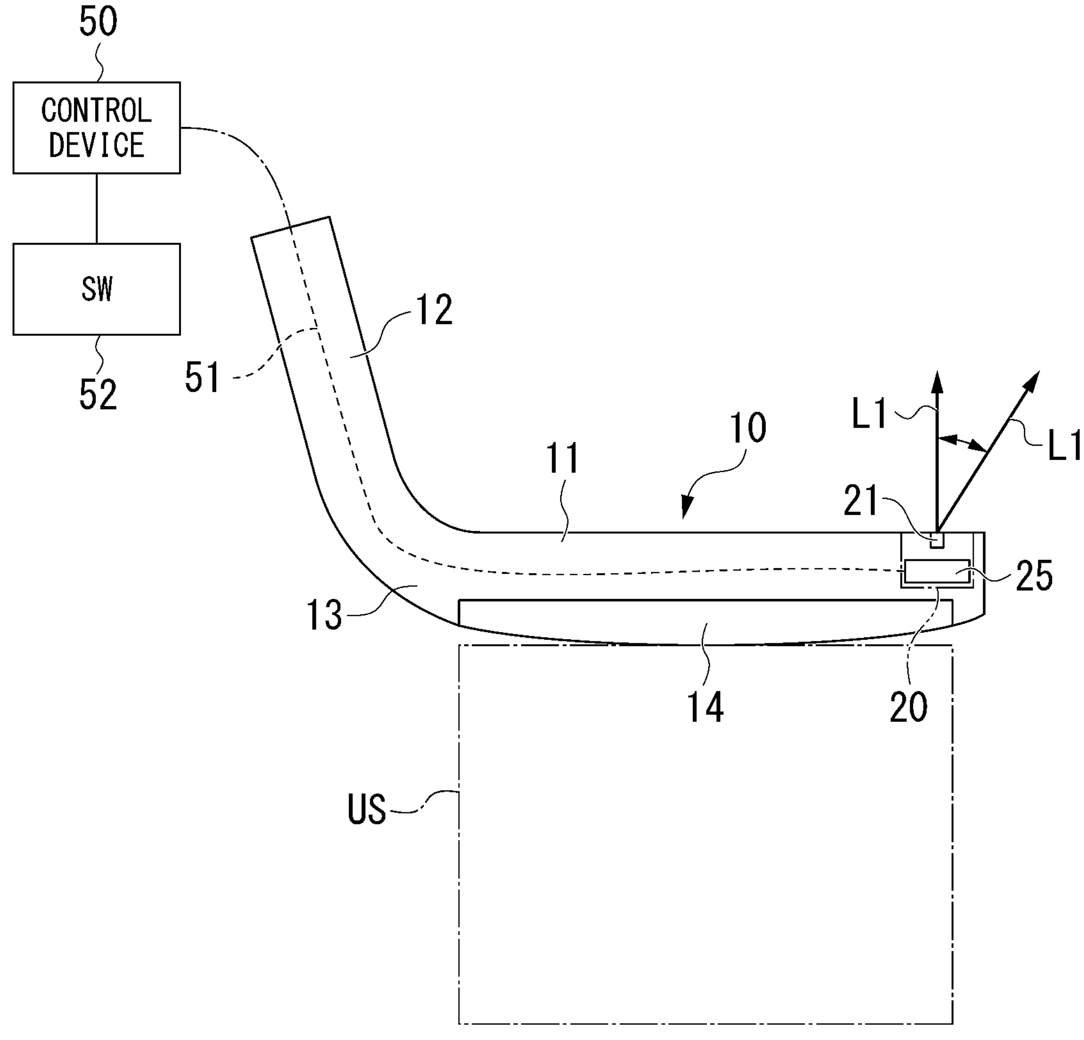
FIG. 8 is a diagram showing a state of an ultrasonic probe 10 of a third embodiment viewed from the side.

Next, an ultrasonic probe 10 of a third embodiment will be described. The ultrasonic probe 10 of the third embodiment differs from the first embodiment mainly with respect to the configuration of the radiation part. The third embodiment will be described below focusing on differences from the first embodiment. FIG. 8 is a diagram showing a state of the ultrasonic probe 10 of the third embodiment viewed from the side.

In the third embodiment, the radiation part 20 includes, for example, a first light source 21 and a swinging structure 25. The first light source 21 is configured to be able to swing such that the radiation direction of the first laser beam L1 radiated by the first light source 21 moves between a first direction and a second direction. The swinging structure 25 swings the first light source 21 such that the first light source 21 can radiate the first laser beam L1 in a direction between the first direction and the second direction.

A drive source, for example, a motor, is connected to the swinging structure 25, and the swinging structure 25 is driven by the motor. The motor may be provided inside the transmitting/receiving head 11 or may be provided outside the transmitting/receiving head 11. In a case in which the motor is provided outside the transmitting/receiving head 11, the driving force of the motor may be transmitted to the swinging structure 25 via a transmission mechanism or the like.

A control device 50 similar to that of the first embodiment is connected to the radiation part 20 via a wire 51, and a switch 52 is connected to the control device 50. A practitioner can operate the first light source 21 or stop the operation of the first light source 21 by operating the switch 52 and can also cause the swinging structure 25 to swing the first light source 21 or stop swinging.

Figure 9:
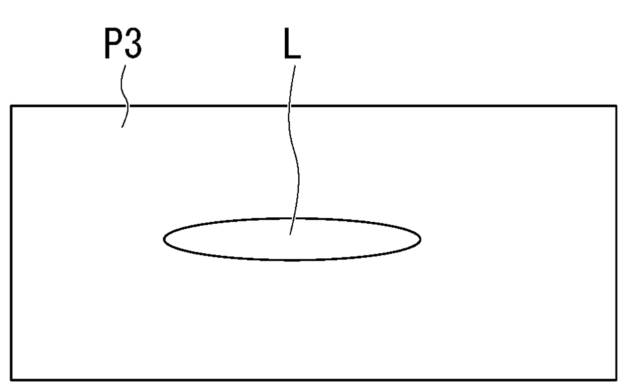
FIG. 9 is a diagram showing a state in which a laser beam L is radiated to the body surface P3 in the third embodiment.

FIG. 9 is a diagram showing a state in which a laser beam L is radiated to the body surface P3 in the third embodiment. When the swinging structure 25 swings the first light source 21 while the first light source 21 is actuated, the laser beam L is displayed such that it forms an ellipse having a straight line connecting the first direction and the second direction as a long diameter on the body surface P3.

The ultrasonic probe 10 of the third embodiment has the same effects as the ultrasonic probe 10 of the first embodiment. Furthermore, in the ultrasonic probe 10 of the third embodiment, the radiation part 20 includes a swinging structure 25 that swings the first light source 21. Therefore, the first light source 21 can radiate the laser beam L in both the first direction and the second direction. Further, the swinging structure 25 swings the first light source 21 while the first light source 21 is actuated such that an ellipse having a straight line connecting the first direction and the second direction as a long diameter is displayed, and thus the position of the puncture hole 15 and the position where the puncture needle 30 will be inserted can be easily ascertained.

Fourth Embodiment

Next, an ultrasonic probe 10 of a fourth embodiment will be described. The ultrasonic probe 10 of the fourth embodiment differs from the first embodiment mainly with respect to the configuration of the radiation part and inclusion of an invisible light detection device. The fourth embodiment will be described below focusing on differences from the first embodiment.

Figure 10:
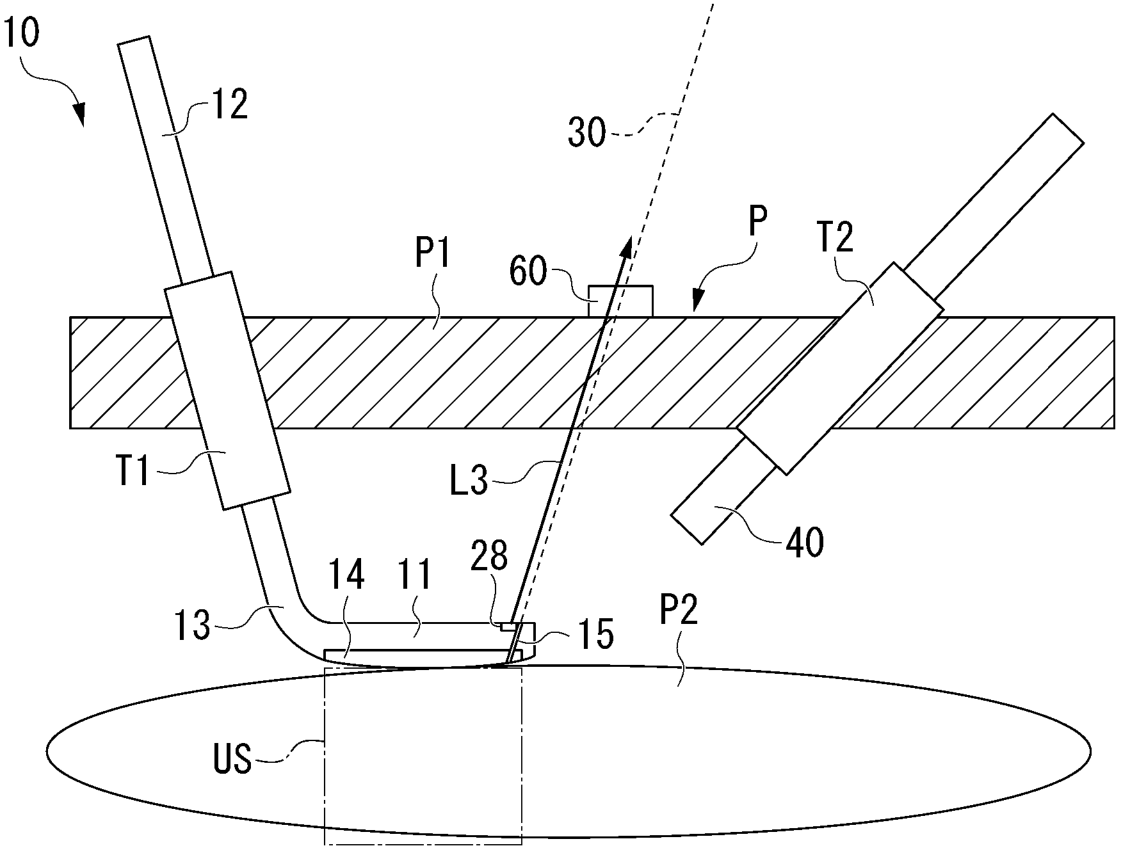
FIG. 10 is a diagram showing a state of an ultrasonic probe 10 of a fourth embodiment viewed from the side.

FIG. 10 is a diagram showing a state of the ultrasonic probe 10 of the fourth embodiment viewed from the side. The ultrasonic probe 10 of the fourth embodiment includes a radiation part 28 that radiates a laser beam L3 which is invisible light having wavelengths outside of 400 nm to 700 nm, for example. The radiation part 28 radiates the laser beam L3 in a first direction.

An invisible light detection device 60 is provided at a position on the body surface P3 of the subject P in the first direction when viewed from the radiation part 28. When the invisible light detection device 60 senses invisible light, it outputs a detection sound to notify detection of the invisible light. Instead of or in addition to outputting a detection sound, the invisible light detection device 60 may notify detection of invisible light by, for example, lighting or blinking a lamp, displaying information on a display, actuating a vibrator, or the like.

For example, at the time of inserting the puncture needle 30, a practitioner places the invisible light detection device 60 on the body surface P3. The practitioner moves the invisible light detection device 60 along the surface of the body surface P3 until the invisible light detection device 60 detects invisible light and outputs a detection sound. Thereafter, the invisible light detection device 60 outputs a detection sound, thereby notifying that the invisible light detection device 60 is in the first direction when viewed from the radiation part 28 on the body surface P3. The practitioner can recognize the position of the puncture hole 15 based on the position of the invisible light detection device 60 at this time.

In the ultrasonic probe 10 of the fourth embodiment, the practitioner can recognize the position of the puncture hole 15 based on the position of the invisible light detection device 60. Therefore, the ultrasonic probe 10 of the fourth embodiment can make it easier for the practitioner to insert the puncture needle 30. Furthermore, the ultrasonic probe 10 of the fourth embodiment allows the practitioner to recognize the position of the puncture hole 15 by the invisible light detection device 60 detecting invisible light. Therefore, even if the skin on the body surface P3 is thick and does not allow visible light to pass through, for example, the position of the puncture hole 15 can be easily recognized by the practitioner. As a result, the practitioner can easily insert the puncture needle 30.

Although the invisible light detection device 60 is placed on the body surface P3 of the subject P in the fourth embodiment, the invisible light detection device 60 may be placed at another position. The invisible light detection device may be provided, for example, on glasses worn by the practitioner. In this case, the practitioner can easily recognize the position of the puncture hole 15 without moving the invisible light detection device by hands or the like and thus can easily insert the puncture needle 30.

Furthermore, in the fourth embodiment, the radiation part 28 may radiate invisible light in the second direction in addition to the first direction, and the invisible light detection device that detects the invisible light radiated in the second direction may be mounted on the body surface P3 or may be provided on the glasses worn by the practitioner. In this case, as in the first embodiment, the position at which the puncture needle 30 will be inserted on the body surface P3 of the subject P can be confirmed. Therefore, it is possible to make it easier for the practitioner to insert the puncture needle 30.

In a case in which the radiation part radiates a plurality of laser beams in each of the above embodiment, the laser beams are the same laser beams, but the modes of the plurality of laser beams may be different. For example, the plurality of laser beams may have different colors, shapes, sizes, and the like. Further, in a case in which a plurality of laser beams is radiated in the second direction, the modes of the laser beams radiated in the second direction may be the same and may be different from the mode of a laser beam radiated in the first direction.

Further, although the radiation part 20 radiates laser beams in the first direction and the second direction in the first to third embodiments described above, the radiation part 20 may radiate laser beams in either the first direction or the second direction. At the time of radiating laser beams in the first direction and the second direction, the laser beams may be radiated in both directions at the same time, or the laser beams may be radiated at different timings.

According to at least one embodiment described above, it is possible to make it easier to insert a puncture needle by including a head part having a puncture guide for guiding a puncture needle, an acoustic emission part that is provided in the head part and emits ultrasonic waves, and a radiation part that radiates laser beams in a first direction opposite to a direction in which the acoustic emission part emits the ultrasonic waves and in a second direction different from the first direction.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasonic probe to be introduced into a body of a subject, the ultrasonic probe comprising:

a head part having a puncture guide configured to guide a puncture needle;

an acoustic emission part provided in the head part and configured to emit ultrasonic waves; and a radiation part configured to radiate laser beams including a first laser beam in a first direction and a second laser beam in a second direction different from the first direction, the first direction being opposite to a direction in which the acoustic emission part emits the ultrasonic waves and being directed to a body surface of the subject in the body of the subject, the second direction being a direction along an extending direction of the puncture guide, the first direction being different from the direction along the extending direction of the puncture guide, wherein the radiation part is further configured to always radiate the first laser beam and the second laser beam.

2. The ultrasonic probe according to claim 1, wherein the radiation part comprises a first light source configured to radiate the first laser beam in the first direction and a second light source configured to radiate the first laser beam in the second direction.

3. The ultrasonic probe according to claim 2, wherein the second light source is configured to radiate the second laser beam in a plurality of second directions.

4. The ultrasonic probe according to claim 3, wherein the second light source comprises a plurality of light sources, each of the plurality of light sources being configured to radiate the second laser beam in each of the plurality of second directions.

5. The ultrasonic probe according to claim 1, wherein the radiation part further comprises a light source configured to radiate a laser beam, and a designation structure configured to designate a direction in which the laser beam is radiated by the light source from among a plurality of directions.

6. The ultrasonic probe according to claim 1, wherein the radiation part further comprises a swinging structure configured to swing a light source to enable the first laser beam to be radiated in a direction between the first direction and the second direction.

* * * * *